(12) United States Patent
D'Ambrosio et al.

(10) Patent No.: US 9,522,081 B2
(45) Date of Patent: *Dec. 20, 2016

(54) METHODS AND DEVICES FOR BRAIN COOLING FOR TREATMENT AND/OR PREVENTION OF EPILEPTIC SEIZURES

(75) Inventors: Raimondo D'Ambrosio, Seattle, WA (US); Jason Fender, Bonney Lake, WA (US); Jeffrey Ojemann, Seattle, WA (US); John W. Miller, Bellevue, WA (US); Matthew Smyth, Frontenac, MO (US); Steven M. Rothman, Clayton, MO (US)

(73) Assignees: University of Washington, Seattle, WA (US); Washington University, St. Louis, MO (US); Regents of the University of Minnesota, Minneapolis, MN (US)

(*) Notice: Subject to any disclaimer, the term of this patent is extended or adjusted under 35 U.S.C. 154(b) by 1241 days.

This patent is subject to a terminal disclaimer.

(21) Appl. No.: 13/482,903

(22) Filed: May 29, 2012

(65) Prior Publication Data

US 2012/0290052 A1    Nov. 15, 2012

Related U.S. Application Data

(63) Continuation-in-part of application No. 12/629,863, filed on Dec. 2, 2009, now Pat. No. 8,591,562.

(Continued)

(51) Int. Cl.
*A61F 7/12* (2006.01)
*A61F 7/00* (2006.01)
*A61F 7/02* (2006.01)

(52) U.S. Cl.
CPC .......... *A61F 7/12* (2013.01); *A61F 2007/0002* (2013.01); *A61F 2007/0096* (2013.01); *A61F 2007/0247* (2013.01)

(58) Field of Classification Search
CPC ................ A61F 7/12; A61F 2007/0002; A61F 2007/0247

See application file for complete search history.

(56) References Cited

U.S. PATENT DOCUMENTS

| 4,041,956 | A | * | 8/1977 | Purdy | .................... | A61N 1/375 607/36 |
| 4,940,052 | A | | 7/1990 | Mann | | |

(Continued)

FOREIGN PATENT DOCUMENTS

| JP | 2007-209523 | 8/2007 |
| WO | WO99/34758 | 7/1999 |

OTHER PUBLICATIONS

Alán et al. "Absolute levels of transcripts for mitochondrial uncoupling proteins UCP2, UCP3, UCP4, and UCP5 show different patterns in rat and mice tissues," Journal of Bioenergetics and Biomembranes, 41(1):71-78, (Feb. 2009).

(Continued)

*Primary Examiner* — Kaitlyn Smith
(74) *Attorney, Agent, or Firm* — K&L Gates LLP

(57) ABSTRACT

Passive prosthetic devices for focally cooling a brain and methods for inhibiting seizures are disclosed. The prosthetic devices replace a thermally insulating bone flap with a thermally conductive insert having an inner surface that contacts the relatively warm meninges or brain and an outer surface that contacts the relatively cool scalp. In an embodiment, the prosthesis is unitary; in another, a biocompatible casing is filled with a highly conductive core; in another, a filled polymer block is attached to a plate; and in another, the bone flap is filled with a conductive polymer. In one embodiment, a filled polymer containing elements that exhibit the magnetocaloric effect provide heat transfer that can be enhanced by application of a suitable magnetic field. Focal (Continued)

cooling as low as 1.2° C. has been found effective at inhibiting seizures.

39 Claims, 5 Drawing Sheets

Related U.S. Application Data

(60) Provisional application No. 61/491,139, filed on May 27, 2011, provisional application No. 61/119,295, filed on Dec. 2, 2008.

(56) References Cited

U.S. PATENT DOCUMENTS

| | | |
|---|---|---|
| 5,311,876 A | 5/1994 | Olsen |
| 5,429,582 A | 7/1995 | Williams |
| 5,611,767 A | 3/1997 | Williams |
| 6,022,308 A | 2/2000 | Williams |
| 6,083,148 A | 7/2000 | Williams |
| 6,146,411 A | 11/2000 | Noda |
| 6,248,126 B1 | 6/2001 | Lesser et al. |
| 6,364,899 B1 | 4/2002 | Dobak, III |
| 6,506,189 B1 | 1/2003 | Rittman, III |
| 6,629,990 B2 | 10/2003 | Putz |
| 6,648,907 B2* | 11/2003 | Larnard ............ A61F 7/12 607/105 |
| 6,652,566 B2* | 11/2003 | Larnard ............ A61F 7/12 607/105 |
| 6,660,026 B2* | 12/2003 | Larnard ............ A61F 7/12 128/898 |
| 6,743,200 B2* | 6/2004 | Larnard ............ A61F 7/12 604/103.07 |
| 6,793,670 B2 | 9/2004 | Osorio et al. |
| 6,849,072 B2 | 2/2005 | Lee et al. |
| 6,899,726 B2* | 5/2005 | Larnard ............ A61F 7/12 607/104 |
| 6,923,826 B2* | 8/2005 | Larnard ............ A61F 7/12 607/105 |
| 6,978,183 B2 | 12/2005 | Rothman |
| 6,986,783 B2 | 1/2006 | Gunn |
| 7,004,961 B2 | 2/2006 | Wong |
| 7,094,234 B1 | 8/2006 | Lennox |
| 7,156,867 B2 | 1/2007 | Lennox |
| 7,204,833 B1 | 4/2007 | Osorio et al. |
| 7,228,171 B2 | 6/2007 | Lesser et al. |
| 7,229,468 B2 | 6/2007 | Wong, Jr. |
| 7,529,586 B2 | 5/2009 | Wahlstrand |
| 8,140,152 B2 | 3/2012 | John |
| 8,202,308 B2 | 6/2012 | Smyth |
| 8,267,983 B2 | 9/2012 | Rogers et al. |
| 8,478,419 B2 | 7/2013 | Pless et al. |
| 8,591,562 B2 | 11/2013 | D'Ambrosio et al. |
| 8,761,889 B2 | 6/2014 | Wingeier et al. |
| 8,938,290 B2 | 1/2015 | Wingeier et al. |
| 8,965,513 B2 | 2/2015 | Wingeier et al. |
| 8,968,377 B2* | 3/2015 | Boyden ............ 607/108 |
| 2002/0077682 A1* | 6/2002 | Lee ............ A61F 7/12 607/113 |
| 2003/0014097 A1 | 1/2003 | Putz et al. |
| 2003/0195588 A1 | 10/2003 | Fischell et al. |
| 2003/0225442 A1* | 12/2003 | Saadat ............ A61F 7/12 607/105 |
| 2004/0049250 A1 | 3/2004 | Lamard et al. |
| 2004/0082984 A1 | 4/2004 | Osorio et al. |
| 2005/0149123 A1 | 7/2005 | Lesser |
| 2005/0222652 A1* | 10/2005 | Mori ............ A61F 7/12 607/105 |
| 2005/0273144 A1 | 12/2005 | Lennox |
| 2006/0173522 A1 | 8/2006 | Osorio |
| 2007/0213784 A1 | 9/2007 | Pless |
| 2007/0225781 A1* | 9/2007 | Saadat ............ A61F 7/12 607/105 |
| 2007/0282405 A1* | 12/2007 | Wong ............ A61F 7/12 607/104 |
| 2008/0077211 A1* | 3/2008 | Levinson ............ A61F 7/10 607/108 |
| 2008/0140149 A1 | 6/2008 | John |
| 2008/0183097 A1 | 7/2008 | Leyde et al. |
| 2008/0264464 A1 | 10/2008 | Lee et al. |
| 2009/0005843 A1 | 1/2009 | Smyth |
| 2009/0112273 A1 | 4/2009 | Wingeier |
| 2009/0112277 A1 | 4/2009 | Wingeier |
| 2009/0112278 A1 | 4/2009 | Wingeier et al. |
| 2009/0112279 A1 | 4/2009 | Wingeier |
| 2009/0112280 A1 | 4/2009 | Wingeier |
| 2009/0222059 A1 | 9/2009 | Hillis |
| 2010/0198204 A1 | 8/2010 | Rogers |
| 2010/0274237 A1 | 10/2010 | Yamakawa et al. |
| 2010/0312318 A1 | 12/2010 | D'Ambrosio et al. |
| 2011/0172554 A1 | 7/2011 | Leyde et al. |
| 2011/0201944 A1 | 8/2011 | Higgins et al. |
| 2011/0213222 A1 | 9/2011 | Leyde et al. |
| 2012/0290051 A1* | 11/2012 | Boyden ............ A61N 5/025 607/113 |
| 2012/0290052 A1 | 11/2012 | D'Ambrosio et al. |
| 2012/0310313 A1 | 12/2012 | Rogers et al. |

OTHER PUBLICATIONS

André et al. "Pathogenesis and pharmacology of epilepsy in the lithium-pilocarpine model," Epilepsia, 48(Suppl 5):41-47, (Sep. 2007).

Annegers et al. "A population-based study of seizures after traumatic brain injuries," New England Journal of Medicine, 338(1):20-24, (Jan. 1998).

Annegers et al. "Causes of epilepsy: contributions of the Rochester epidemiology project," Mayo Clinic Proceedings, 71(6):570-575, (Jun. 1996).

Aronica et al. "Inflammation in epilepsy: clinical observations," Epilepsia, 52(Suppl 3):26-32, (May 2011).

Atkins et al. "Post-traumatic seizure susceptibility is attenuated by hypothermia therapy," European Journal of Neuroscience, 32(11):1912-1920, (Dec. 2010).

Author Unknown, Collaborative Group for the Study of Epilepsy "Prognosis of epilepsy in newly referred patients: a multicenter prospective study of the effects of monotherapy on the long-term course of epilepsy," Epilepsia, 33(1):45-51, (Jan. 1992).

Bagić et al. "Towards a non-invasive interictal application of hypothermia for treating seizures: a feasibility and pilot study," Acta Neurologica Scandinavica, 118(4):240-244, (Oct. 2008).

Baldwin et al "Effect of hypothermia on epileptiform activity in the primate temporal lobe," Science, 124(3228):931-932, (Nov. 1956).

Bancaud et al "Clinical semiology of frontal lobe seizures," in Advances in Neurology, eds. P. Chauvel et al., Raven Press: NY, 57:3-58, (1992).

Beghi, "Overview of studies to prevent posttraumatic epilepsy," Epilepsia, 44(Suppl 10):21-26, (Oct. 2003).

Berg et al. "Early development of intractable epilepsy in children: a prospective study," Neurology, 56(11):1445-1452, (Jun. 2001).

Bialer et al. "Progress report on new antiepileptic drugs: a summary of the Tenth Eilat Conference (Eilat X)," Epilepsy Research, 92(2-3):89-124, (Dec. 2010).

Bittar, et al "Time-dependent reversal of long-term potentiation by brief cooling shocks in rat hippocampal slices," Brain Research, 620(2): 181-188, (Aug. 1993).

Brengelmann "Specialized brain cooling in humans?" The FASEB Journal, 7(12):1148-1153, (Sep. 1993).

Callaghan et al. "Likelihood of seizure remission in an adult population with refractory epilepsy," Annals of Neurology, 62(4):382-389, (Oct. 2007).

Cereghetti et al. "Phagocytosis: coupling of mitochondrial uncoupling and engulfment," Current Biology, 21(20):R852-R854, (Oct. 2011).

Ceulemans et al. "The dual role of the neuroinflammatory response after ischemic stroke: modulatory effects of hypothermia," Journal of Neuroinflammation, 7:74, 18 pages, (Nov. 2010).

(56) References Cited

OTHER PUBLICATIONS

Charlebois et al. "Metabolic heat production as a measure of macrophage response to particles from orthopedic implant materials," Journal of Biomedical Materials Research, 59(1):166-175, (Jan. 2002).
Choi et al. "Role of brain inflammation in epileptogenesis," Yonsei Medical Journal, 49(1):1-18, (Feb. 2008).
Christian et al. "A review of selective hypothermia in the management of traumatic brain injury," Neurosurgical Focus, 25(4):E9, 8 pages, (Oct. 2008).
Clifton et al. "Lack of effect of induction of hypothermia after acute brain injury," New England Journal of Medicine, 344(8):556-563, (Feb. 2001).
Corry et al. "Hypothermia for refractory status epilepticus," Neurocritical Care, 9(2):189-197, (Apr. 2008).
D'Ambrosio et al. "Mild passive focal cooling prevents epileptic seizures after head injury in rats," Annals of Neurology, 73(2):199-209, (Feb. 2013).
D'Ambrosio et al. "Posttraumatic Epilepsy Following Fluid Percussion Injury in the Rat," Abstract #P127 from the 21st Annual National Neurotrauma Society Symposium, Journal of Neurotrauma, 20(10):1059, (Oct. 2003).
D'Ambrosio et al., "What is an epileptic seizure? Unifying definitions in clinical practice and animal research to develop novel treatments," Epilepsy Currents, 10(3):61-66, (May-Jun. 2010).
Davidson, et al. "Measurement of thermal conductivity of bovine cortical bone," Medical Engineering & Physics, 22(10):741-747 (Dec. 2000).
Diaz-Arrastia et al. "Neurophysiologic and neuroradiologic features of intractable epilepsy after traumatic brain injury in adults," Archives of Neurology, 57(11):1611-1616, (Nov. 2000).
Diaz-Arrastia et al. "Posttraumatic epilepsy: the endophenotypes of a human model of epileptogenesis," Epilepsia, 50(Suppl 2):14-20, (Feb. 2009).
Dietrich, et al "The evidence for hypothermia as a neuroprotectant in traumatic brain injury," Neurotherapeutics, 7(1):43-50, (Jan. 2010).
Eastman et al. "Antiepileptic and Antiepileptogenic Performance of Carisbamate after Head Injury in the Rat: Blind and Randomized Studies," Journal of Pharmacology and Experimental Therapeutics, 336(3):779-790, (Mar. 2011).
Eastman et al. "ECoG studies of valproate, carbamazepine and halothane in frontal lobe epilepsy induced by head injury in the rat," Experimental Neurology, 224(2):369-388, (Aug. 2010).
Elting et al. "Mild hypothermia for refractory focal status epilepticus in an infant with hemimegalencephaly," European Journal of Paediatric Neurology, 14(5):452-455, (Sep. 2010).
Essman, et al "Audiogenic seizure in genetically susceptible mice: relation of hypothermia to onset and susceptibility," Experimental Neurology, 9(3):228-235, (Mar. 1964).
Fabene et al. "A role for leukocyte-endothelial adhesion mechanisms in epilepsy," Nature Medicine, 14(12):1377-1383, (Dec. 2008).
François et al. "Carisbamate has powerful disease-modifying effects in the lithium-pilocarpine model of temporal lobe epilepsy," Neuropharmacology, 61(1-2):313-328, (Jul.-Aug. 2011).
French, "Refractory epilepsy: clinical overview," Epilepsia, 48(Suppl 1):3-7, (Mar. 2007).
Frey, "Epidemiology of posttraumatic epilepsy: a critical review," Epilepsia, 44(Suppl 10):11-17, (Oct. 2003).
Burton, J.M., et al., "Transcortical Cooling Inhibits Hippocampal-Kindled Seizures in the Rat," Epilepsia 46(12):1881-1887, Dec. 2005.
D'Ambrosio, R., et al., "Functional Definition of Seizure Provides New Insight Into Post-Traumatic Epileptogenesis," Brain 132(10):2805-2821, Oct. 2009.
D'Ambrosio, R., et al., "Post-Traumatic Epilepsy Following Fluid Percussion Injury in the Rat," Brain 127(2):304-314, Feb. 2004.

D'Ambrosio, R., et al., "Progression From Frontal-Parietal to Mesial-Temporal Epilepsy After Fluid Percussion Injury in the Rat," Brain 128(1):174-188, Jan. 2005.
Gasteiger, E.L., et al., "Interictal Afterdischarge in Focal Penicillin Epilepsy: Block by Thalamic Cooling," Experimental Neurology 88(2):349-359, May 1985.
Gluckman, P.D., et al., "Selective Head Cooling With Mild Systemic Hypothermia After Neonatal Encephalopathy: Multicentre Randomised Trial," Lancet 365(9460):663-670, Feb. 2005.
Karkar, K.M., et al., "Comment Letters: Focal Cooling Suppresses Spontaneous Epileptiform Activity Without Changing the Cortical Motor Threshold," Epilepsia 43(8):932-935, Aug. 2002.
Karlov, V.A., "Focal Cooling Suppresses Continued Activity of Epileptic Focus in Patients With Partial Status Epilepticus," Epilepsia 44(12):1605, Dec. 2003.
Sartorius, C.J., and M.S. Berger, "Rapid Termination of Intraoperative Stimulation-Evoked Seizures With Application of Cold Ringer's Lactate to the Cortex: Technical Note," Journal of Neurosurgery 88(2):349-351, Feb. 1998.
Shankaran, S., et al., "Whole-Body Hypothermia for Neonates With Hypoxic-Ischemic Encephalopathy," New England Journal of Medicine 353(15):1574-1584, Oct. 2005.
Testa, G., and P. Gloor, "Generalized Penicillin Epilepsy in the Cat: Effect of Midbrain Cooling," Electroencephalography and Clinical Neurophysiology 36(5):517-524, May 1974.
Yang, X.-F., and S.M. Rothman, "Focal Cooling Rapidly Terminates Experimental Neocortical Seizures," Annals of Neurology 49(6):721-726, Jun. 2001.
Yang, X.-F., et al., "Neocortical Seizure Termination by Focal Cooling: Temperature Dependence and Automated Seizure Detection," Epilepsia 43(3):240-245, Mar. 2002.
Friedman et al. "Blood-brain barrier breakdown-inducing astrocytic transformation: novel targets for the prevention of epilepsy," Epilepsy Res., 85(2-3):142-149, (Aug. 2009).
Friedman et al. "Molecular cascades that mediate the influence of inflammation on epilepsy," Epilepsia, 52(Suppl 3):33-39, (May 2011).
Fujii et al. "Cooling of the epileptic focus suppresses seizures with minimal influence on neurological functions," Epilepsia, 53(3):485-493, (Mar. 2012).
Geering et al. "Peculiarities of cell death mechanisms in neutrophils," Cell Death and Differentiation, 18(9):1457-1469, (Sep. 2011).
Gonzalez-Ibarra et al. "Therapeutic hypothermia: critical review of the molecular mechanisms of action," Frontiers in Neurology, 2:4, 8 pages, (Feb. 2011).
Gorman et al. "The effects of local cooling of the cortical surface on the motor cortex response following stimulation of the pyramidal tract," Electroencephalography and Clinical Neurophysiology, 23(4):360-370, (Oct. 1967).
Grujicic et al. "The effect of thermal contact resistance on heat management in the electronic packaging," Applied Surface Science, 246(1-3):290-302, (Jun. 2005).
Hachimi-Idrissi et al. "Postischemic mild hypothermia reduces neurotransmitter release and astroglial cell proliferation during reperfusion after asphyxial cardiac arrest in rats," Brain Research, 1019(1-2):217-225, (Sep. 2004).
Hayatsu et al. "Heat production as a quantitative parameter of phagocytosis," Journal of Immunological Methods, 109(2):157-160, (May 1988).
Hayatsu et al. "Heat production due to intracellular killing activity," Tokai Journal of Experimental and Clinical Medicine, 15(5):395-399, (Sep. 1990).
Hitiris et al. "Predictors of pharmacoresistant epilepsy," Epilepsy Research, 75(2-3):192-196, (Jul. 2007).
Hudak et al. "Evaluation of seizure-like episodes in survivors of moderate and severe traumatic brain injury," Journal of Head Trauma Rehabilitation, 19(4):290-295, (Jul.-Aug. 2004).
Ivens et al. "TGF-beta receptor-mediated albumin uptake into astrocytes is involved in neocortical epileptogenesis," Brain, 130(Pt 2):535-547, (Feb. 2007).

(56) References Cited

OTHER PUBLICATIONS

Jiang et al. "Effect of long-term mild hypothermia or short-term mild hypothermia on outcome of patients with severe traumatic brain injury," Journal of Cerebral Blood Flow and Metabolism, 26(6):771-776, (Jun. 2006).
Kelly et al. "Photothrombotic brain infarction results in seizure activity in aging Fischer 344 and Sprague Dawley rat," Epilepsy Research, 47(3):189-203, (Dec. 2001).
Kharatishvili et al. "A model of posttraumatic epilepsy induced by lateral fluid-percussion brain injury in rats," Neuroscience, 140(2):685-697, (Jun. 2006).
Kharlamov et al. "Electrobehavioral characteristics of epileptic rats following photothrombotic brain infarction," Epilepsy Research, 56(2-3):185-203, (Oct. 2003).
Kuhl et al. "Prophylaxis of posttraumatic seizures," Annals of Pharmacotherapy, 24(3):277-285, (Mar. 1990).
Langer et al. "Therapeutic window of opportunity for the neuroprotective effect of valproate versus the competitive AMPA receptor antagonist NS1209 following status epilepticus in rats," Neuropharmacology, 61(5-6):1033-1047, (Oct.-Nov. 2011).
Lee et al. "Capsaicin prevents kainic acid-induced epileptogenesis in mice," Neurochemistry International, 58(6):634-640, (May 2011).
Leppik "The classification of seizures," in Contemporary diagnosis and management of the patient with epilepsy. Handbooks in Health Care, . IE Leppik, ed., Newton: Pennsylvania, pp. 8-15, (1997).
Li et al. "Cytokines and epilepsy," Seizure, 20(3):249-256, (Apr. 2011).
Li et al. "Hemicooling of the brain by carotid-carotid perfusion," Experimental Neurology, 20(4):533-543, (Apr. 1968).
Linares et al. "Hypothermia for the treatment of ischemic and hemorrhagic stroke," Critical Care Medicine, 37(7 Suppl):S243-S249, (Jul. 2009).
Liu et al. "Effects of selective brain cooling in patients with severe traumatic brain injury: a preliminary study," Journal of International Medical Research, 34(1):58-64, (Jan.-Feb. 2006).
Lotocki et al. "Alterations in blood-brain barrier permeability to large and small molecules and leukocyte accumulation after traumatic brain injury: effects of post-traumatic hypothermia," Journal of Neurotrauma, 26(7):1123-1134, (Jul. 2009).
Lu et al. "Efficacy of topiramate in adult patients with symptomatic epilepsy: an open-label, long-term, retrospective observation," CNS Drugs, 23(4):351-359; (2009), retrieved Aug. 2015.
Marion et al. "Current and future role of therapeutic hypothermia," Journal of Neurotrauma, 26(3):455-467, (Mar. 2009).
Marks et al. "Seizure localization and pathology following head injury in patients with uncontrolled epilepsy," Neurology, 45(11):2051-2057, (Nov. 1995).
Meador "The basic science of memory as it applies to epilepsy," Epilepsia, 48(Suppl 9):23-25, (Dec. 2007).
Mori et al. "Effects of mild (33 degrees C) and moderate (29 degrees C) hypothermia on cerebral blood flow and metabolism, lactate, and extracellular glutamate in experimental head injury," Neurological Research, 20(8):719-726, (Dec. 1998).
Mori et al. "Temporal profile of changes in brain tissue extracellular space and extracellular ion (Na(+), K(+)) concentrations after cerebral ischemia and the effects of mild cerebral hypothermia," Journal of Neurotrauma, 19(10):1261-1270, (Oct. 2002).
Moseley et al. "Unit activity during focal cortical hypothermia in the normal cortex," Experimental Neurology, 37(1):152-163, (Oct. 1972).
Nalivaeva et al. "Sodium valproate: an old drug with new roles," Trends in Pharmacological Sciences, 30(10):509-514, (Oct. 2009).
Oakley et al. "Temperature- and age-dependent seizures in a mouse model of severe myoclonic epilepsy in infancy," Proceedings of the National Academy of Sciences USA, 106(10):3994-3999, (Mar. 2009).
Oby et al "The blood-brain barrier and epilepsy," Epilepsia, 47(11):1761-1774, (Nov. 2006).
Oku et al. "The influence of focal brain cooling on neurophysiopathology: validation for clinical application," Journal of Neurosurgery, 110(6):1209-1217, (Jun. 2009).
Ommaya et al. "Extravascular local cooling of the brain in man," Journal of Neurosurgery, 20(1):8-20, (Jan. 1963).
Ooboshi et al. "Hypothermia inhibits ischemia-induced efflux of amino acids and neuronal damage in the hippocampus of aged rats," Brain Research, 884(1-2):23-30, (Nov. 2000).
Osorio et al. "Seizure control with thermal energy? Modeling of heat diffusivity in brain tissue and computer-based design of a prototype mini-cooler," Epilepsy & Behavior, 16(2):203-211, (Oct. 2009).
Owens "Effect of hypothermia on seizures induced by physical and chemical means," American Journal of Physiology, 193(3):560-562, (Jun. 1958).
Park et al. "Continued clearance of apoptotic cells critically depends on the phagocyte Ucp2 protein," Nature, 477(7363):220-224, (Aug. 2011).
Pärsson et al. "Metabolic response of granulocytes and platelets to synthetic vascular grafts: preliminary results with an in vitro technique," Journal of Biomedical Materials Research, 29(4):519-525, (Apr. 1995).
Peterson et al. "Hypothermia treatment for traumatic brain injury: a systematic review and meta-analysis," Journal of Neurotrauma, 25(1):62-71, (Jan. 2008).
Polderman "Mechanisms of action, physiological effects, and complications of hypothermia," Critical Care Medicine, 37(7 Suppl):S186-S202, (Jul. 2009).
Qiu et al. "Effects of therapeutic mild hypothermia on patients with severe traumatic brain injury after craniotomy," Journal of Critical Care, 22(3):229-235, (Sep. 2007).
Rakhade et al. "Development of later life spontaneous seizures in a rodent model of hypoxia-induced neonatal seizures," Epilepsia, 52(4):753-765, (Apr. 2011).
Ravizza et al. "Inflammation and prevention of epileptogenesis," Neuroscience Letters, 497(3):223-230, (Jun. 2011).
Rothman "The therapeutic potential of focal cooling for neocortical epilepsy," Neurotherapeutics, 6(2):251-257, (Apr. 2009).
Rothman et al. "Focal cooling for epilepsy: An alternative therapy that might actually work," Epilepsy and Behavior, 7:214-221, (Sep. 2005).
Rupprecht et al. "Quantification of uncoupling protein 2 reveals its main expression in immune cells and selective up-regulation during T-cell proliferation," PLoS One, 7(8):e41406, (Aug. 2012).
Sahuquillo et al. "Cooling the injured brain: how does moderate hypothermia influence the pathophysiology of traumatic brain injury," Current Pharmaceutical Design, 13(22):2310-2322, (2007).
Seiffert et al. "Lasting blood-brain barrier disruption induces epileptic focus in the rat somatosensory cortex," Journal of Neuroscience, 24(36):7829-7836, (Sep. 2004).
Semah et al. "Is the underlying cause of epilepsy a major prognostic factor for recurrence?" Neurology, 51(5):1256-1262, (Nov. 1998).
Sick et al. "Mild hypothermia improves recovery of cortical extracellular potassium ion activity and excitability after middle cerebral artery occlusion in the rat," Stroke, 30(11):2416-2421, (Nov. 1999).
Sloviter "Progress on the issue of excitotoxic injury modification vs. real neuroprotection; implications for post-traumatic epilepsy," Neuropharmacology, 61(5-6):1048-1050, (Oct.-Nov. 2011).
Smyth et al. "Focal Cooling Devices for the Surgical Treatment of Epilepsy," Neurosurgery Clinics of North America, 22(4):533-546, (Oct. 2011).
Sourek et al. "General and local hypothermia of the brain in the treatment of intractable epilepsy," Journal of Neurosurgery, 33(3):253-259, (Sep. 1970).
Stewart et al. "Chronic dysfunction of astrocytic inwardly rectifying K+ channels specific to the neocortical epileptic focus after fluid percussion injury in the rat," Journal of Neurophysiology, 104(6):3345-3360, (Dec. 2010).
Stewart et al. "Development of postinfection epilepsy after Theiler's virus infection," Journal of Neuropathology and Experimental Neurology, 69(12):1210-1219, (Dec. 2010).

(56) References Cited

OTHER PUBLICATIONS

Suzuki et al. "Infrared thermal imaging of rat somatosensory cortex with whisker stimulation," Journal of Applied Physiology, 112(7):1215-1222, (Apr. 2012).
Temkin "Preventing and treating posttraumatic seizures: the human experience," Epilepsia, 50(Suppl 2):10-13, (Feb. 2009).
Tokutomi et al. "Effect of 35 degrees C hypothermia on intracranial pressure and clinical outcome in patients with severe traumatic brain injury," Journal of Trauma, 66(1):166-173, (Jan. 2008).
Tolias et al. "Critical appraisal of neuroprotection trials in head injury: what have we learned?" NeuroRx, 1(1):71-79, (Jan. 2004).
U.S. Appl. No. 61/491,139, filed May 27, 2011 titled, "Passive Cooling Prosthesis," to D'Ambrosio et al.
Van Der Worp et al. "Hypothermia in animal models of acute ischaemic stroke: a systematic review and meta-analysis," Brain, 130(Pt 12):3063-3074, (Dec. 2007).
Vezzani et al. "The role of inflammation in epilepsy," Nature Reviews Neurology, 7(1):31-40, (Jan. 2011).
Wang et al. "Hypothermia Reduces Brain Edema, Spontaneous Recurrent Seizure Attack, and Learning Memory Deficits in the Kainic Acid Treated Rats," CNS Neuroscience and Therapeutics, 17(5):271-280, (Oct. 2011).
Wang et al. "Valproic acid attenuates blood-brain barrier disruption in a rat model of transient focal cerebral ischemia: The roles of HDAC and MMP-9 inhibition," Journal of Cerebral Blood Flow and Metabolism, 31(1):52-57, (Jan. 2011).
White "Animal models of epileptogenesis," Neurology, 59(9 Supp 5):S7-S14, (Nov. 2002).
Williams et al. "A chronic histopathological and electrophysiological analysis of a rodent hypoxic-ischemic brain injury model and its use as a model of epilepsy," Neuroscience, 149(4):943-961, (Nov. 2007).
Williamson et al. "Clinical and EEG features of complex partial seizures of extratemporal origin," Epilepsia, 27(Suppl 2):S46-S63, (Aug. 1986).
Williamson et al. "Complex partial seizures of frontal lobe origin," Annals of Neurology, 18(4):497-504, (Oct. 1985).
Wohlrab et al. "Benign focal epileptiform discharges in children after severe head trauma: prognostic value and clinical course," Epilepsia, 38(3):275-278, (Mar. 1997).
Yamamura et al. "Heat production as a quantitative parameter for cell differentiation and cell function," Tokai Journal of Experimental and Clinical Medicine, 15(5):377-380, (Sep. 1990).
Yang et al. "Cooling produces minimal neuropathology in neocortex and hippocampus," Neurobiology of Disease, 23(3):637-643, (Sep. 2006).
Zattoni et al. "Brain infiltration of leukocytes contributes to the pathophysiology of temporal lobe epilepsy," Journal of Neuroscience, 31(11):4037-4050, (Mar. 2011).
Zhao et al. "General versus specific actions of mild-moderate hypothermia in attenuating cerebral ischemic damage," Journal of Cerebral Blood Flow and Metabolism, 27(12):1879-1894, (Dec. 2007).
Imoto et al, "Use of a Peltier chip with a newly devised local brain-cooling system for neocortical seizures in the rat, Technical note," Journal of Neurosurgery, vol. 104 pp. 150-156, (Jan. 2006).
Tanaka et al, "Effective suppression of hippocampal seizures in rats by direct hippocampal cooling with a Peltier chip," Journal of Neurosurgery, vol. 108, pp. 791-797, (Apr. 2008).
Curia et al. "Impact of injury Location and Severity on Post-traumatic Epilepsy in the Rat: Role of Frontal Neocortex," Cerebral Cortex, 21(7):1574-1592, (Jul. 2011).

\* cited by examiner

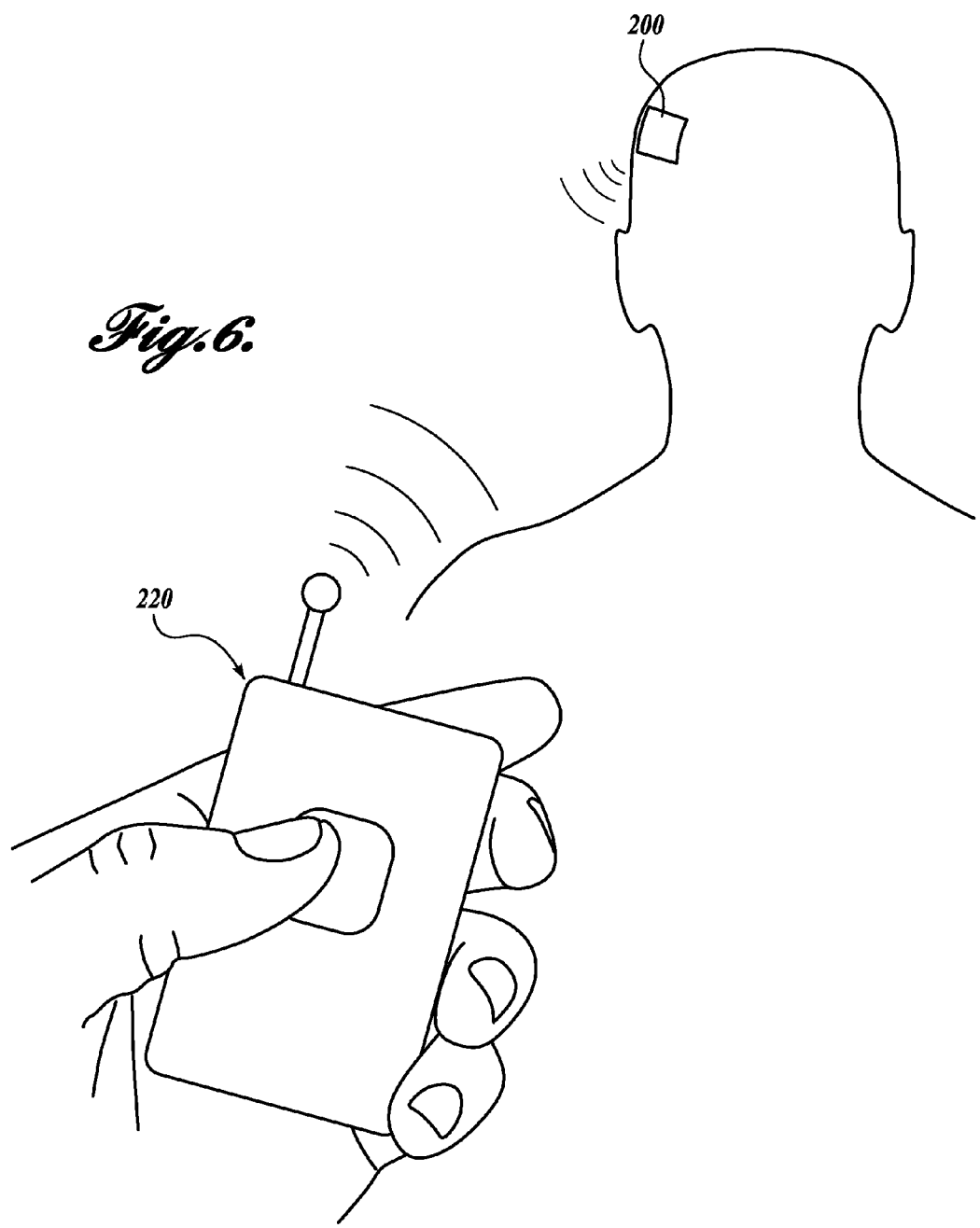

METHODS AND DEVICES FOR BRAIN COOLING FOR TREATMENT AND/OR PREVENTION OF EPILEPTIC SEIZURES

CROSS-REFERENCES TO RELATED APPLICATIONS

This application claims the benefit of Provisional Application No. 61/491,139, filed May 27, 2011, and is a continuation-in-part of Ser. No. 12/629,863, now U.S. Pat. No. 8,591,562, filed Dec. 2, 2009, which claims the benefit of Provisional Application No. 61/119,295, filed Dec. 2, 2008, the entire disclosures of which are each hereby incorporated by reference herein.

STATEMENT OF GOVERNMENT LICENSE RIGHTS

This invention was made with government support under NS053928, 5R01NS053928-02, and 7R01NS042936-06 awarded by the National Institutes of Health, and W81XWH-05-2-0072 awarded by the U.S. Army Medical Research & Material Command. The government has certain rights in the invention.

BACKGROUND

Epilepsy is best understood as a syndrome involving episodic abnormal electrical activity in the brain, or epileptic seizures, that result from abnormal, excessive or hypersynchronous neuronal activity in the brain. It is estimated that 50 million people worldwide have epilepsy. The onset of epileptic symptoms occurs most frequently in infants and the elderly, and may also arise from trauma to the brain or as a consequence of brain surgery.

Epileptic symptoms are sometimes controllable with medication. However, nearly one-third (⅓) of persons with epilepsy cannot control seizures even with the best available medications. In certain cases, neurosurgery is undertaken to remove the epileptic focus to control the seizures.

For example, the high incidences of traumatic brain injury (TBI) in both the civilian and military populations, and the absence of any prophylactic treatment for acquired epilepsy, such as posttraumatic epilepsy (PTE), create an urgent need to develop broad-spectrum and easily deployable therapeutic strategies. There are currently no effective means for preventing the onset of PTE following head injury. The administration of anticonvulsants after head injury may decrease early posttraumatic seizures but has failed to impact the development of long-term epilepsy or improve the incidence of disability or death. Therefore, novel treatment paradigms are needed.

Several in vitro and in vivo studies have demonstrated that brain cooling by 10-20° C. reduces epileptiform activity in seizure models and in humans. Technologies based on cranially implanted Peltier (thermoelectric) cells powered by batteries have been considered to achieve such a high degree of cooling in the brain.

The process of epileptogenesis in humans is not known. It is theorized that agents that are neuroprotective may also be antiepileptogenic. Similarly, the process of ictogenesis (i.e., the precipitation of seizures) is not necessarily the same as epileptogenesis. It is therefore entirely possible that treatments that prevent the precipitation of seizures do not prevent the genesis of epilepsy and, vice versa, those that may prevent the onset of epilepsy may not be capable of shutting down existing seizures.

There are known devices that use active cooling to shut down epileptic seizures (antiepileptic effect). Known devices are based on the assumption that cooling a targeted area of the brain by about 10° C. is necessary to shut down the epileptic focus. One such device is based on active Peltier cells that cool the brain, including heat pipes to cool deep into the brain. A second exemplary known device uses circulating coolant in tubing implanted within the dorsal hippocampus of a brain to achieve cooling of at least 7° C. in the hippocampus. Unfortunately, such devices are typically highly intrusive (if inserted deep into the brain) and require the implantation of complex structures (e.g., heat pipes), electronics (Peltier elements), and long-lasting powering elements (e.g., batteries) to produce the necessary cooling. None of the known methods and devices provide continuous prevention of epilepsy (epileptogenesis) but only provide remedial action when a seizure begins so as to lessen the severity of the seizure.

What is desired, therefore, is an improved device for preventing and/or treating acquired epilepsy.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A fully implantable cooling device for providing focal cooling to a brain is disclosed that includes a thermally conductive prosthesis sized and configured to be inserted into an aperture formed in a skull, and configured such that an inner surface of the prosthesis contacts the brain or meninges, and an outer surface contacts a corresponding portion of the scalp. The implanted device replaces a thermally insulating bone section with a thermally conductive prosthesis to cool the contacted portion of the brain.

In an embodiment, the prosthesis may be configured such that it does not penetrate the meninges, and may optionally further comprise subcutaneous and/or subcranial cooling strips. In an alternative embodiment, the prosthesis may include a heat pipe or other highly conductive probe that extends from the inner surface of the prosthesis into the brain adjacent an epileptic focus.

In an embodiment, the prosthesis comprises a biocompatible casing, for example titanium, stainless steel, or polymer, and a thermally conductive core, for example aluminum, copper, or stainless steel. In an alternative embodiment, the prosthesis is of unitary construction.

In an embodiment, the prosthesis comprises an inner portion, for example a block of a matrix material, for example silicone, containing a plurality of embedded thermally conductive elements, and an outer plate that engages the skull. Alternatively, the prosthesis may comprise a bone flap removed from the skull and modified to incorporate a thermally conductive matrix material extending through the bone flap, and contacting the brain or meninges and the scalp. The embedded thermally conductive elements may be diamond, graphene, gadolinium or other magnetocaloric material, carbon nanotubes, copper beads or the like.

A method for inhibiting epileptic seizures is disclosed comprising removing a portion of a skull to form a recess, and implanting a thermally conductive passive cooling device, for example a device in accordance with those described above, and having an inner surface that contacts the brain or meninges, and an outer surface that contacts the scalp, to cool the contacted portion of the brain.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 6 illustrates the brain-cooling device shown in FIG. 4 or FIG. 5 and using a filled polymer with elements that exhibit the magnetocaloric effect, and further including a device for generating a magnetic field that interacts with the magnetocaloric elements.

DETAILED DESCRIPTION

Figure 1:
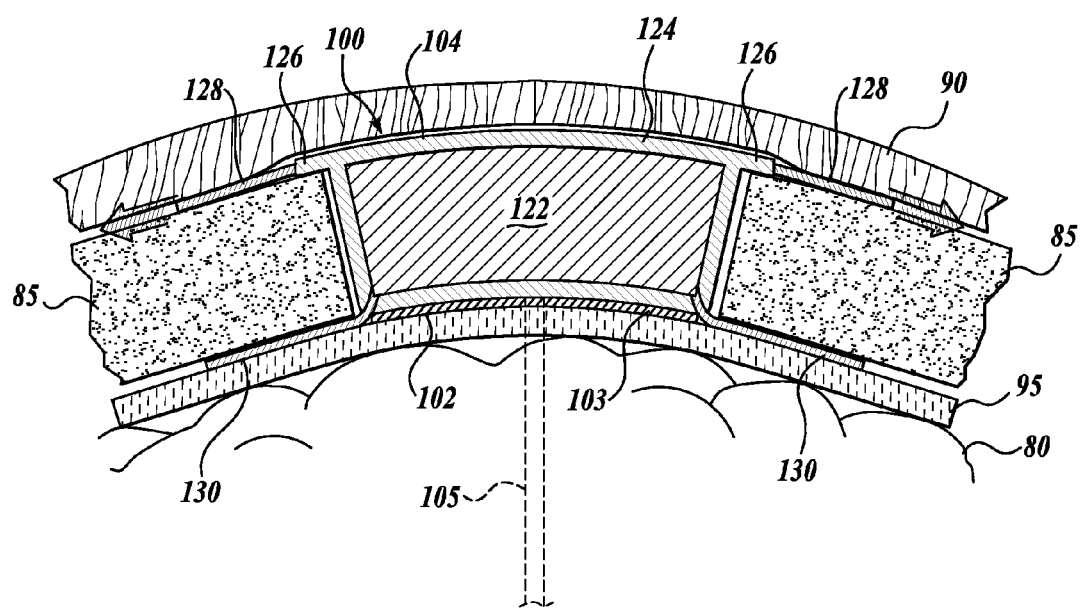
FIG. 1 is a partial cross-sectional view of a representative brain-cooling device in accordance with the present invention.

Studies have suggested that cooling of the brain can assist in providing remedial effects to victims of epilepsy. Although a specific acquired epilepsy referred to herein as posttraumatic epilepsy (PTE) is relatively common, it will be appreciated that the provided embodiments are also effective in treating other types of epilepsy (e.g., reflex epilepsy, traumatic epilepsy resulting from stroke, epilepsy resulting from cerebrovascular disease, etc.). Prior art techniques have focused on a large degree of cooling (e.g., greater than 8° C.) and typically involve embedding active cooling devices deep within the brain (e.g., in the medial temporal lobe). Additionally, known methods focus on reducing the severity of a seizure after it has begun as opposed to preventing epileptogenesis using prophylactic measures, as provided herein.

The present inventors have developed a novel in vivo model of PTE in rats wherein chronic recurrent spontaneous partial seizures appear after a single event of a clinically relevant model of concussive closed head injury referred to as a fluid percussion injury (FPI). This model represents a significant departure from previous models of acquired epilepsy because the initiating insult, a transient compression of the meninges without penetration, is mechanically very similar to human cases of concussive closed head injury. In a recently completed blind, randomized preclinical study, the present inventors made the remarkable discovery that certain epileptic seizures can be prevented by very mild cooling of the surface of the injured brain in the region of the epileptic focus or injury. Positive results were found with focal cooling as low as just ~1.2° C. These studies indicate that very mild focal cooling of portions of the neocortex, which may be maintained for a significant period of time, can reduce the risk of epileptic seizures in patients suffering from head injuries or the like. Unlike the relatively large degree of cooling suggested by the prior art, the mild cooling disclosed herein may be achieved using a passive cooling system.

In laboratory experiments, an implanted cooling device in accordance with the present invention have been found to significantly reduce the development of epileptic seizures. The implanted device produces a mild focal cooling of the neocortex (brain) through the meninges, for example, producing a localized cooling ($\Delta T$) of less than 4° C. and even less than 2° C. The mild cooling indicated by the present invention can be accomplished with an extradural focal cooling device, i.e., without penetration of the meninges.

While passive heat transfer devices described herein are generally in contact with the meninges, it is contemplated that the device may alternatively be placed in contact with the brain itself. It will be appreciated, for example, that traumatic injuries to the central nervous system may rupture the meninges, and such a rupture site would be a potential area for use of the provided methods and devices. Thus, if the meninges are compromised, the provided embodiments can be used directly on the subdural central nervous system (e.g., neocortex of the brain).

As used herein, the cooling produced by the disclosed devices is defined to be the difference between the core temperature of the patient and the temperature measured at the interface of the patient and the inner surface of the cooling device.

Disclosed herein is a novel cooling device, specifically designed to perform cooling of the central nervous system, for neuroprotective, antiepileptogenic, and antiepileptic treatments. In the current embodiment, the cooling device is implanted in a recess sized and configured by removal of a portion of a patient's neurocranium or skull. As used herein, the terms "skull" and "cranium" are defined to mean the neurocranium or braincase, i.e., the portion of the skull that houses the brain. The embedded cooling device may be formed, for example, to fit in the location of a craniotomy or a decompressive craniectomy, and to achieve the desired degree of cooling. A heat-collecting internal surface of the device is placed in contact with the patient's meninges or brain. Optionally, flexible heat-conducting strips may be used to increase the heat transfer to the cooling device and/or to provide cooling to regions of the brain adjacent the site of the craniotomy.

After the desired cooling course of treatment, the cooling device may be removed and replaced by bone or plates, as per accepted current procedures. In some situations it may be preferable to leave the cooling device implanted permanently, or for an extended period of time, to allow for periodic cooling treatment.

The present invention provides methods for brain cooling to prevent epileptogenesis after brain injuries, methods for passive brain cooling to prevent ictogenesis and/or epileptogenesis, and devices for passive brain cooling.

A brain-cooling device in accordance with the teachings of the present invention will now be described further with reference to the FIGURES, wherein like numbers indicate like parts. FIG. 1 shows a fully implanted passive focal brain-cooling device 100 in accordance with the present invention implanted in a patient. The focal brain-cooling device 100 is sized and configured to be inserted into a recess formed by removal of a portion of the patient's neurocranium 85, such that the device 100 contacts the meninges 95, preferably without significantly compressing the meninges 95. Although direct contact with the meninges 95 is currently preferred, it is contemplated that the device 100 may alternatively be placed in direct contact with the brain 80 (e.g., neocortex), for example, if an injury has ruptured the meninges 95.

The cranium 85 is a flat bone comprising a thick outer layer of compact tissue, a relatively thin and brittle inner layer of compact tissue, and an inner layer of cancellous tissue called the diploë. The cranium 85 is a good thermal insulator and therefore aids in maintaining the brain 80 at the relatively higher temperature, relative to the scalp. The human brain 80 typically maintains a temperature approximately equal to, or slightly greater than, the body core temperature. The scalp 90, by contrast, is typically several degrees cooler than the body's core temperature, although the scalp temperature will generally vary much more than the core temperature, and is more subject to environmental conditions. The human scalp is actively cooled though perspiration, and has among the highest density of eccrine sweat glands in the human body.

As noted in *Specialized brain cooling in humans?*, G. L. Brengelmann, The FASEB Journal Vol. 7, 1148-1153 (September 1993), "The few measurements of human brain temperature available support the concept that this large organ is at nearly uniform temperature, slightly above arterial temperature and not directly influenced by head surface temperature." Although tympanic temperature falls when the face or neck are cooled, the tympanic temperature does not reflect brain temperature.

The focal brain-cooling device 100 is a thermally conductive device that replaces a small section of the thermally insulating cranium 85. The inner surface 102 of the device 100 contacts the relatively warm meninges 95 (or the brain 80) and the outer surface 104 contacts the relatively cool scalp 90. The device 100 therefore provides focal cooling to the region of the brain 80 adjacent the device 100 by increasing the heat transfer between the adjacent portion of the brain 80 and the scalp 90.

The focal brain-cooling device 100 in this embodiment includes a core 122 made of a highly thermally conductive material, and an outer casing 124 made of a thermally conductive biocompatible material. Representative core 122 materials include aluminum, copper, stainless steel, and other materials having high thermal mass and/or high thermal conductivity. The outer casing 124 may be a biocompatible metal, such as titanium, stainless steel, or a non-metallic biocompatible material known to those of skill in the art (e.g., biocompatible polymers). Alternatively the focal brain-cooling device 100 may conveniently be formed unitarily, for example, of stainless steel or titanium. A unitary construction requires both high thermal mass/conductivity and biocompatibility.

In a current embodiment, the inner surface 102 comprises a relatively soft and pliable material layer 103 having good thermal conductivity that is affixed to the outer casing 124. The inner layer 103 is conformable to optimize the contact between the inner surface 102 and the meninges 95. For example, the pliable layer 103 may be formed from a "soft" polymer such as a silicone (e.g., a polysiloxane).

The outer surface 104 of the outer casing 124 is substantially rigid and extends longitudinally beyond the aperture formed in the cranium 85 to define a protective rim or wings 126, such that the device 100 is precisely positioned with respect to the brain 80 and is prevented from being inadvertently inserted too far into the recess or inadvertently urged toward the brain, undesirably compressing the meninges 95 and/or brain 80.

FIG. 1 also shows optional heat-dissipating subcutaneous strips 128, which are formed from a thermally conductive, biocompatible material, and are fixed to the outer casing 124. The subcutaneous strips 128 increase the effective area of the outer surface 104 in contact with the relatively low temperature scalp 90, thereby improving heat transfer through the device 100.

Optional heat-collecting subcranial strips 130 are also fixed to the outer casing 124. The subcranial strips 130 are flexible, and may be similar in construction to the subcutaneous strips 128 discussed above, and/or may provide a mesh, webbing, or stripping extending out from the core 122 to cover a larger area of the meninges 95 to improve cooling efficiency. The subcranial strips 130 are sized and configured to be inserted beneath the cranium 85, adjacent the aperture formed in the cranium 85. The subcranial strips 130 may be extradural (i.e., disposed strictly between the cranium 85 and the meninges 95) or transdural (i.e., extending at least partially through the meninges 95). The subcranial strips 130 are good thermal conductors and are formed to be biocompatible.

In addition to increasing the net heat transfer through the device 100, the subcranial strips 130 may also be used to expand or shift the location of the focal cooling. In some situations, it may be desirably to provide focal cooling to a location on the brain 80 that is near or adjacent to the aperture formed in the cranium 85. For example, typically after removing a portion of the cranium 85, additional testing is conducted to more precisely identify the epileptic focus within the brain 80. If the epileptic focus is not directly beneath the cranial aperture, the subcranial strips 130 may be used to expand or shift the location of the cooling affect, without requiring any additional removal of cranial material. For example, the subcranial strips 130 allow the surgeon to more precisely locate the cooled region of the brain 80 to more closely correspond to the epileptic focus.

In another option, illustrated in FIG. 1, a small-diameter heat pipe 105 (shown in phantom) extends from the inner surface 102 into the patient's brain 80. The heat pipe 105 is sized and configured to extend to the epileptic focus. The heat pipe 105 (or more than one heat pipe) may be particularly useful in cases in which the epileptic focus is in a region of the brain that is not easily accessed, such as the ventral frontal or temporal lobe.

Figure 2A:
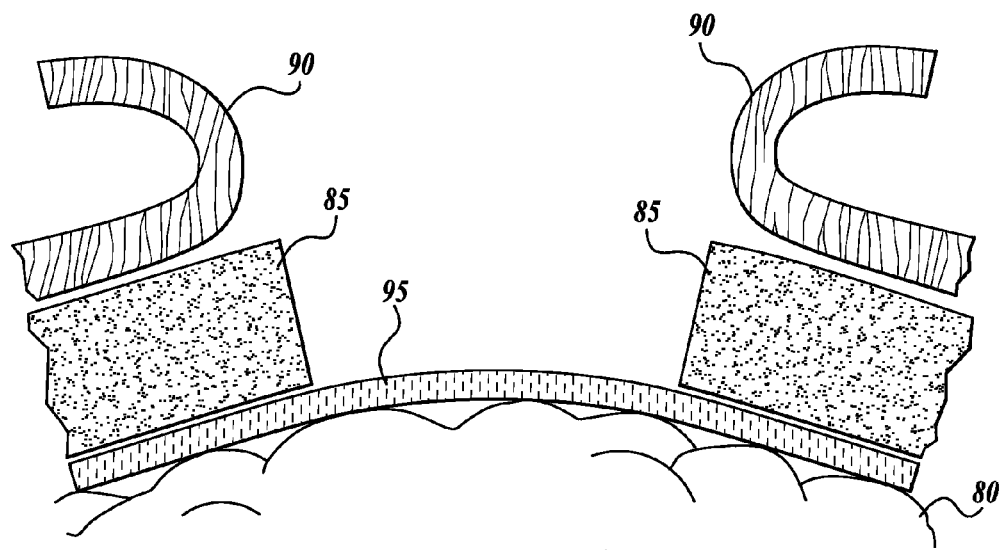
FIGS. 2A-2C illustrate implantation of the brain-cooling device shown in FIG. 1.
Figure 2B:
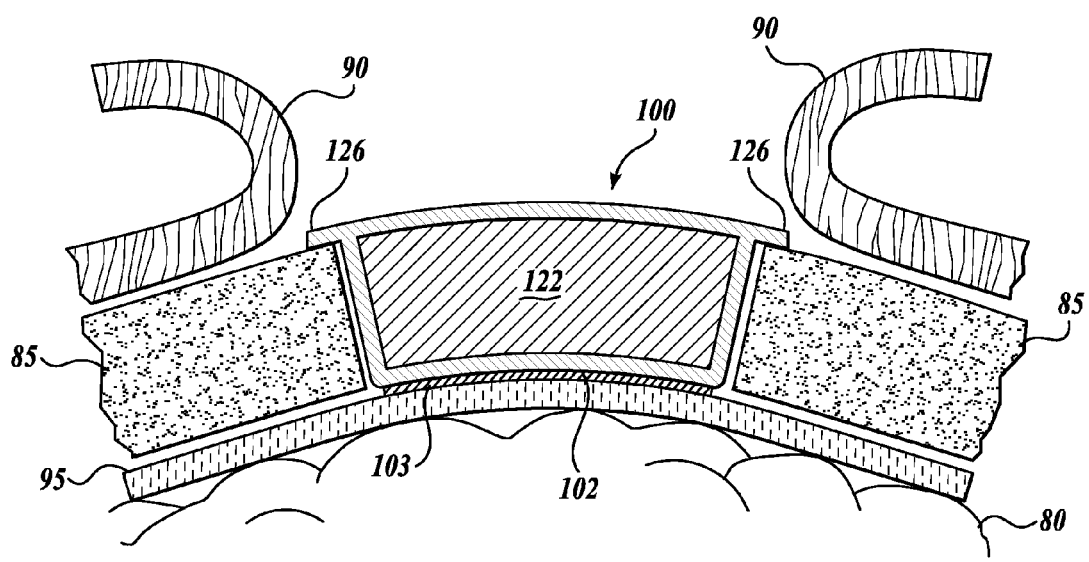
Figure 2C:
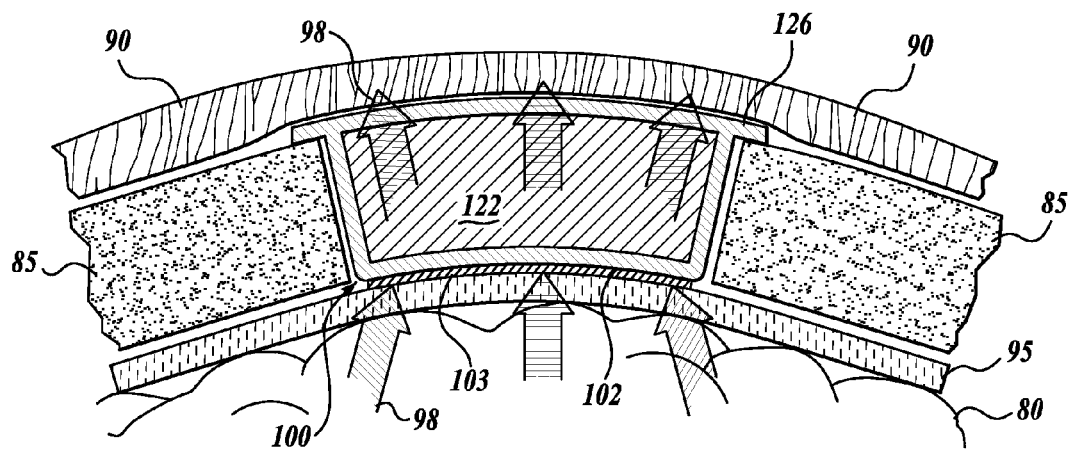

FIGS. 2A-2C illustrate steps for implanting the focal brain-cooling device 100, with the optional cooling strips 128 and 130 removed for clarity. FIG. 2A illustrates schematically a craniotomy site prepared for implanting the device, wherein a bone flap, i.e., a portion of the cranium 85, has been removed. Generally a surgeon or other medical practitioner will first identify a location on the brain 80 for which focal cooling is indicated. The precise location for bone removal and the desired angle of access may then be determined, for example, using various medical imaging technologies, for example, magnetic resonance imaging or the like. The patient's head is prepared for surgery, and the bone flap is removed to expose a selected portion of the meninges 95. In practice, the surgeon may at this time perform additional testing of the brain, for example, using deep brain stimulation or the like, to verify and/or adjust the optimal location for the cooling device 100, and to determined if subcutaneous strips 128 and/or subcranial strips 130 are indicated.

Referring to FIG. 2B, the cooling device 100 is inserted into the craniotomy site such that the inner layer 103 is adjacent the meninges 95, providing thermal communication between the brain 80 and the cooling device 100 through the meninges 95. If subcutaneous strips 128 and/or subcranial strips 130 are to be used, they would also be suitably positioned as indicated in FIG. 1. The cooling device 100 is inserted such that the protective wings 126 abut the cranium 85 to prevent undue pressure or displacement of the meninges 95 by the cooling device 100.

Referring to FIG. 2C, the scalp 90 is then closed over the cooling device 100 to fully implant the device 100. Heat is conducted by the device 100 from the relatively warm brain 80 (through the meninges 95) to the relatively cool scalp 90, as illustrated with arrows 98.

Figure 3:
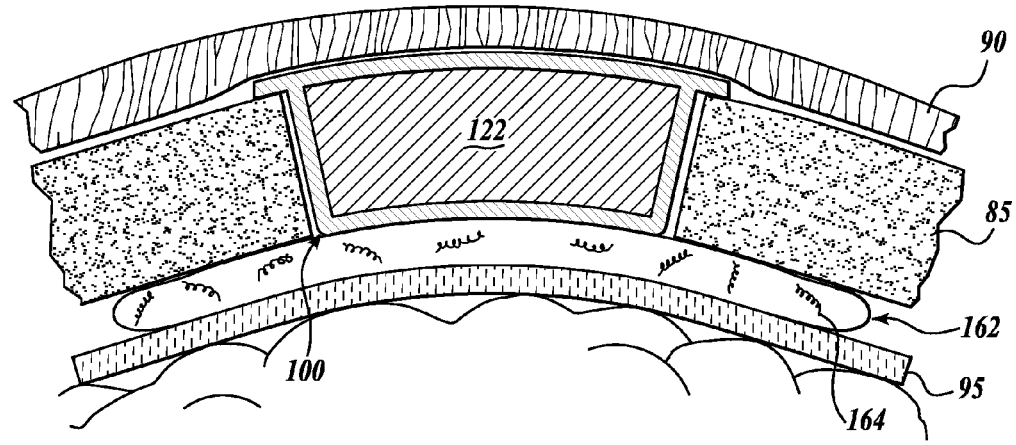
FIG. 3 is a cross-sectional view of the brain-cooling device shown in FIG. 1, with a thermally conductive biocompatible cushion to enhance its heat gathering function.

As shown in FIG. 3, the cooling device 100 may further include a thermally conductive biocompatible cushion 162 to enhance its heat gathering function. In this exemplary embodiment, the cushion 162 includes a silicone sack filled with a fluid (e.g., a saline fluid) and optional thermally conductive filaments 164 (e.g., steel wool). The cushion 162 provides a larger area of contact with the meninges 95 and readily conforms to the meninges 95. The composition of the cushion 162 allows for good thermal transport between the meninges 95 contacted by the cushion 162 and the cooling device 100.

Figure 4:
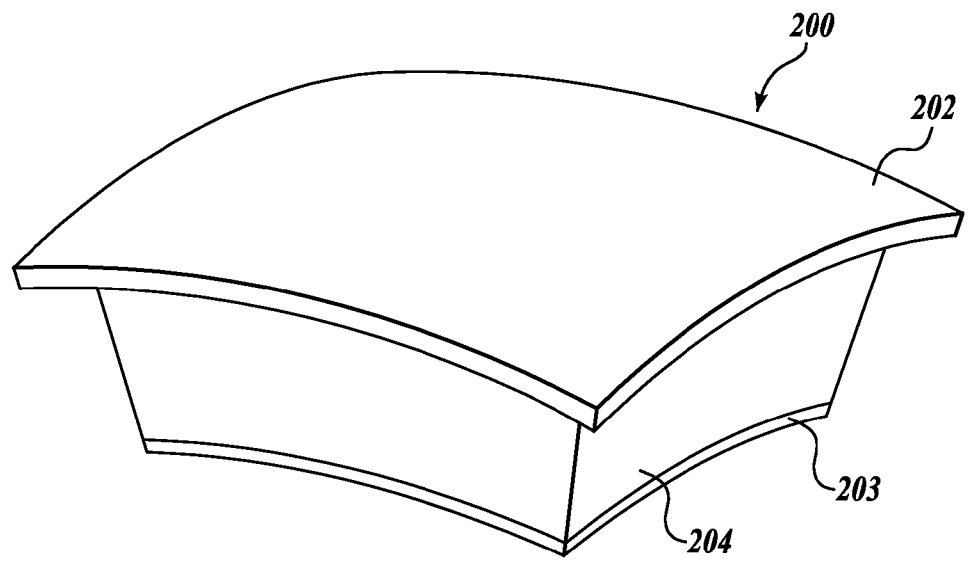
FIG. 4 is a perspective view of a second embodiment of a brain-cooling device in accordance with the present invention having an outer plate fixed to a block-like insert.

Another embodiment of a passive focal brain-cooling device 200 in accordance with the present invention is shown in FIG. 4. In this embodiment, the focal brain-cooling device 200 comprises a relatively rigid plate 202, preferably formed from a high thermal conductivity material. Suitable materials include, for example, titanium, stainless steel, or a non-metallic biocompatible material such as biocompatible polymers. A biocompatible, thermally conductive block 204 is affixed to a lower face of the rigid plate 202. For example, the conductive block 204 may be formed from a soft, biocompatible polymer providing a matrix and having encapsulated therein thermally conductive elements. A polymeric matrix encapsulating thermally conductive elements is referred to herein as a "filled polymer."

In a currently preferred embodiment, the filled polymer is a biocompatible silicone filled with highly conductive elements, for example, diamond, graphene, carbon nanotubes, copper beads, or the like. In particular, a filled silicone with graphene has been found to have very favorable thermal conductivity properties. Optionally, a pliable inner layer 203 may be used to contact the meninges 95 to improve heat transfer to the device 200.

Figure 5:
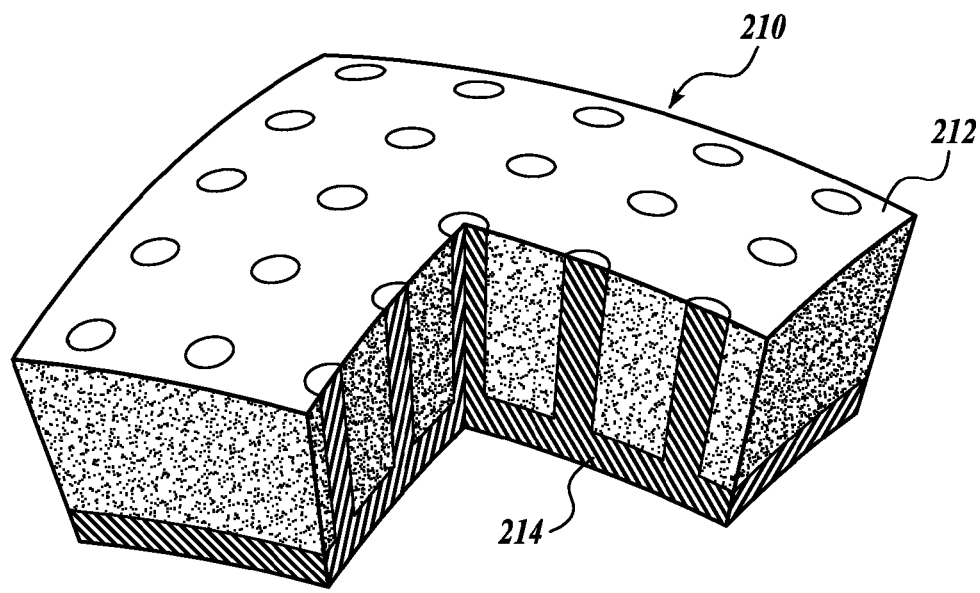
FIG. 5 is a perspective sectional view of a third embodiment of a brain-cooling device in accordance with the present invention formed by modifying a bone flap to incorporate a conductive member extending through the bone flap.

Another embodiment of a passive focal brain-cooling device 210 in accordance with the present invention is shown in FIG. 5, with a portion of the device 210 cut away to show other features. In this embodiment the bone flap 212 (the portion of bone removed in a craniotomy) is retained and used to form the cooling device 210. The bone flap 212 is modified by drilling a plurality of holes through the bone flap 212. A highly thermally conductive component 214 is then formed, for example, by injecting and/or molding a biocompatible polymeric compound filled with high-conductivity elements (e.g., a filled polymer) into the plurality of holes. Preferably, the filled polymer will also be molded along at least a portion of the bottom surface of the bone flap 212 to conformably engage the meninges 95 for a good thermal connection. In other embodiments the polymer may be molded along at least a portion of the top surface of the bone flap 212 to conformably engage the scalp 90 for a good thermal connection. Suitable biocompatible filled polymers include a biocompatible silicone filled with highly conductive elements formed from diamond, graphene, carbon nanotubes, copper beads, or the like.

The devices 200, 210 may optionally utilize subcutaneous strips 128 and/or subcranial strips 130, as discussed above.

The filled polymer components 204, 214, discussed above, may be supplemented or alternatively filled with elements that exhibit the magnetocaloric effect. The magnetocaloric effect is a phenomenon wherein a reversible change in the specific heat of a material can be induced by subjecting the material to a changing magnetic field. For example, gadolinium demonstrates a magnetocaloric effect in which its temperature increases when it enters a magnetic field and decreases when it leaves the magnetic field. The magnetocaloric effect is stronger for the alloy $Gd_5(Si_2Ge_2)$. It is believed that the use of filler elements exhibiting the magnetocaloric effect would allow the cooling effect of the devices to be controlled externally, i.e., by introducing a suitable magnetic field such that it interacts with the cooling devices.

For example, some persons experience warning signs prior to a seizure, such as odd feelings, unusual smells or tastes, confusion, a jerking movement of an extremity, tingling, and/or headaches. As illustrated in FIG. 6, at the first warning sign of a seizure a patient may activate an electromagnetic device 220 that is configured to engage or interact with the magnetocaloric properties of the cooling device 200, to induce the desired focal cooling to prevent or mitigate a seizure.

Any of the fully implanted devices disclosed in accordance with the present invention, e.g., cooling devices 100, 200, 210, may also give the patient the ability to effectively and rapidly provide focal cooling at the first sign of ictogenesis. For example, when a patient first detects a warning sign of the onset of a seizure, the patient may place an ice pack or other cold item against the patient's scalp, over the device 100, 200, or 210, thereby rapidly cooling the region of the neocortex adjacent the device.

While not illustrated, the cooling device internal plate optionally includes a temperature sensor that is operationally connected to an external temperature monitor. In one embodiment, the external temperature monitor is mounted on the brain-cooling device, for example, on the heat-dissipating plate. The temperature sensor optionally includes communication means for transmitting the measured temperature to an off-patient monitoring system (e.g., a computer configured to monitor and log temperature) so as to allow for electronic access, manipulation, and monitoring (e.g., automated notification of doctors if certain temperature thresholds are breached) of the temperature measured by the device.

The present invention provides methods and devices for treating and/or preventing epilepsy. The inventors of the present invention discovered that focal cooling is both antiepileptic and antiepileptogenic. With the employment of seizures induced by a realistic injury, and in the absence of pro-convulsant drugs, it was found that very mild focal cooling of the brain, e.g., by not more than 4° C., and in some embodiments by as little as 1.2° C., is sometimes sufficient to prevent seizures. The finding is notable because it is the first demonstration that minimal (e.g., <2° C.) cooling can prevent or slow down epileptogenesis; and a disease-modifying effect was observed by passive focal cooling at room temperature.

This invention further encompasses novel prosthetic devices specifically designed to perform passive cooling of an injured central nervous system for neuroprotective, anti-epileptogenic, and antiepileptic treatments. Passive brain cooling is not considered in known devices and methods because it has been assumed that therapeutic effects would only be achieved by significant cooling. The below-presented experimental data show otherwise.

The provided device can be removed and replaced by bone or plates, as per accepted current procedures, or left implanted chronically for continuous treatment.

It is also contemplated that the present invention may be employed in a method for treating a patient suffering from a central nervous system injury, wherein the patient has not experienced epileptogenesis, and the method is performed as a prophylactic measure so as to prevent (and/or mitigate) acquired epilepsy and epileptogenesis.

Particular details of experimental animal studies conducted by the present inventors using a novel in vivo model of PTE in rats employing a concussive closed head injury, referred to as a fluid percussion injury (FPI), are provided in the related U.S. Patent Publication No. 2010/0312318, which is hereby incorporated by reference. These details will not be reproduced here, for brevity. The results of the experiments indicate a robust antiepileptogenic effect of focal cooling at modest temperature decreases (e.g., less than 2° C.). Varying magnitudes of focal cooling were applied six days after FPI, and the effect on antiepileptogenesis was recorded. While 100% of animals without focal cooling went on to develop neocortical chronic recurrent spontaneous partial seizures (CRSPSs), only half of the animals focally cooled for three weeks at the injury site developed CRSPSs. In summary, it was determined that a prolonged 1-2° C. focal cooling of the injured neocortex over three weeks post-injury by a passive device is antiepileptogenic, prevents the onset of FPI-induced epilepsy that is resistant to valproate and carbamazepine, and yet is well tolerated by animals, as it does not affect core body temperature and does not induce pathology. Notably, cooling was initiated six days after head injury, and still demonstrated a potent antiepileptogenic effect.

In more recent experiments, the relationship between the cutaneous temperature of the temperature of the neocortex in rats with certain steps taken to more closely reflect physical aspects of human anatomy were studied. The animal skull was first provided with a 6 mm layer of acrylic to simulate the thickness and thermal insulation of a human skull. Four digital thermometers were used to monitor the core temperature (measured rectally), brain epidural temperature under the prosthesis, the scalp temperature, and the scalp cutaneous temperature. For experimental purposes, the cutaneous temperature was clamped using a temperature-controlled metal chamber that was placed in contact with the scalp. the neocortex was cooled with a copper plate prosthesis implanted within a craniotomy site, such that the copper plate was in contact with both the meninges and the overlying scalp. Therefore, while the modified skull effectively insulates the brain from a wide range of temperatures of the scalp, the prosthesis allows controlled focal cooling without affecting the body temperature.

The present invention is not limited to use with PTE sufferers, but can also be extended to other central nervous system injuries that would benefit from local mild cooling of the brain (e.g., stoke victims). The disclosed devices may be particularly beneficial to those suffering from pharmacoresistant neocortical epilepsy. The present invention may be applied as a prophylactic to provide prolonged minimal cooling of the injured brain or epileptic focus, without the undesirable side effects observed in previous clinical trials involving lowering core temperature after head injury or the technological challenges of safely achieving the at least 8-10° C. cooling previously assumed necessary for prevention of epilepsy.

While illustrative embodiments have been illustrated and described, it will be appreciated that various changes can be made therein without departing from the spirit and scope of the invention.

The embodiments of the invention in which an exclusive property or privilege is claimed are defined as follows:

1. An implantable passive cooling device configured to be inserted into an aperture in a skull for focally cooling a brain, the device comprising:
    a passive thermally conductive prosthesis sized and configured to be inserted into an aperture formed in a skull, the prosthesis having an inner surface configured to contact a portion of a meninges or brain disposed in the skull, and an outer surface configured to contact a corresponding portion of a scalp covering the skull;
    wherein the passive thermally conductive prosthesis replaces a thermally insulating bone section to passively produce a focal cooling in the contacted portion of the meninges or brain.

2. The implantable passive cooling device of claim 1, wherein no portion of the prosthesis penetrates the meninges.

3. The implantable passive cooling device of claim 1, wherein the prosthesis further comprises a heat pipe that extends from the prosthesis inner surface and extends to an epileptic focus in the brain.

4. The implantable passive cooling device of claim 1, wherein the prosthesis further comprises at least one thermally conductive subcutaneous strip that extends away from the prosthesis outer surface and is configured to be positioned between the scalp and the skull.

5. The implantable passive cooling device of claim 1, wherein the prosthesis further comprises at least one thermally conductive subcranial strip that extends away from the prosthesis inner surface and is configured to be positioned adjacent the meninges.

6. The implantable passive cooling device of claim 1, wherein the prosthesis comprises a biocompatible outer casing filled with a thermally conductive core.

7. The implantable passive cooling device of claim 6, wherein the biocompatible outer casing comprises one of titanium, stainless steel, and a biocompatible polymer.

8. The implantable passive cooling device of claim 6, wherein the thermally conductive core comprises one of aluminum, copper, and stainless steel.

9. The implantable passive cooling device of claim 1, wherein the thermally conductive prosthesis comprises a unitary insert.

10. The implantable passive cooling device of claim 1, wherein the thermally conductive prosthesis comprises a thermally conductive block disposed between the inner surface of the prosthesis and the outer surface of the prosthesis and an outer plate that is fixed to the thermally conductive block, wherein the outer plate includes the outer surface and wherein the outer plate defines a flange that is configured to engage an outer surface of the skull.

11. The implantable passive cooling device of claim 10, wherein the thermally conductive block includes a biocompatible matrix material having a plurality of thermally conductive elements embedded in the matrix material.

12. The implantable passive cooling device of claim 11, wherein the thermally conductive elements comprise one of diamond, graphene, gadolinium, carbon nanotubes, and copper beads.

13. The implantable passive cooling device of claim 11, wherein the thermally conductive elements comprise a material that exhibits the magnetocaloric effect.

14. The implantable passive cooling device of claim 11, wherein the biocompatible matrix material comprises silicone.

15. The implantable cooling device of claim 11, wherein the biocompatible matrix comprises a polymeric matrix encapsulating the plurality of thermally conductive elements.

16. The implantable passive cooling device of claim 1, wherein the thermally conductive prosthesis comprises a bone flap having a plurality of apertures extending through the bone flap, and a thermally conductive material that fills the plurality of apertures in the bone flap and is configured to contact the meninges or brain.

17. The implantable passive cooling device of claim 16, wherein the thermally conductive material is configured to contact the scalp.

18. The implantable passive cooling device of claim 17, wherein the thermally conductive material comprises a filled polymer comprising a biocompatible polymeric matrix having thermally conductive elements embedded in the polymeric matrix.

19. The implantable passive cooling device of claim 18, wherein the thermally conductive elements comprise one of diamond, graphene, gadolinium, carbon nanotubes, and copper beads.

20. The implantable passive cooling device of claim 18, wherein the thermally conductive elements comprise a material that exhibits the magnetocaloric effect.

21. The implantable passive cooling device of claim 18, wherein the filled polymer further defines the prosthesis inner surface.

22. The implantable passive cooling device of claim 1, wherein the thermally conductive prosthesis cools the contacted portion of the meninges or brain by between 1.2° C. and 4° C.

23. The implantable passive cooling device of claim 1, wherein the thermally conductive prosthesis comprises a biocompatible matrix material having a plurality of thermally conductive elements encapsulated in the matrix material.

24. A method for inhibiting epileptic seizures comprising:
removing a portion of a skull to form a recess over a selected region of a brain;
implanting a thermally conductive passive cooling device into the recess such that an inner surface of the cooling device is in contact with the brain or a meninges surrounding the brain, and an outer surface of the cooling device is in contact with a scalp covering the skull;
wherein the passive cooling device is configured to cool the contacted portion of the meninges or brain.

25. The method of claim 24, wherein no portion of the passive cooling device penetrates the meninges.

26. The method of claim 24, wherein the passive cooling device comprises a biocompatible outer casing and a thermally conductive core.

27. The method of claim 26, wherein the biocompatible outer casing comprises one of titanium, stainless steel, and a biocompatible polymer.

28. The method of claim 26, wherein the core comprises one of aluminum, copper, and stainless steel.

29. The method of claim 24, wherein the passive cooling device comprises a solid, unitary insert.

30. The method of claim 24, wherein the passive cooling device comprises an inner portion and an outer plate that is fixed to the inner portion, wherein the outer plate defines a flange that is configured to engage an outer surface of the skull.

31. The method of claim 30, wherein the inner portion comprises a filled a biocompatible matrix material having thermally conductive elements embedded in the matrix material.

32. The method of claim 30, wherein the thermally conductive elements comprise one of diamond, graphene, carbon nanotubes, gadolinium and copper beads.

33. The method of claim 30, wherein the thermally conductive elements comprise a material that exhibits the magnetocaloric effect.

34. The method of claim 30, wherein the biocompatible matrix material comprises silicone.

35. The method of claim 24, wherein the passive cooling device comprises a bone flap having a plurality of apertures extending through the bone flap, and a filled polymer that fills the plurality of apertures.

36. The method of claim 35, wherein the filled polymer comprises a biocompatible polymeric matrix having thermally conductive elements embedded in the polymeric matrix.

37. The method of claim 36, wherein the thermally conductive elements comprise one of diamond, graphene, carbon nanotubes, gadolinium, and copper beads.

38. The method of claim 37, wherein the thermally conductive elements comprise a material that exhibits the magnetocaloric effect.

39. The method of claim 24 wherein thermally the conductive prosthesis cools the contacted portion of the meninges or brain by between 1.2° C. and 4° C.

* * * * *